(12) United States Patent
Shah et al.

(10) Patent No.: US 8,188,130 B1
(45) Date of Patent: May 29, 2012

(54) ANTI-CANCER HYDANTOIN COMPOUNDS AND METHODS

(75) Inventors: Girish Shah, Monroe, LA (US); Khalid El Sayed, Louisiana, LA (US)

(73) Assignee: University of Louisiana at Monroe, Monroe, LA (US)

( * ) Notice: Subject to any disclaimer, the term of this patent is extended or adjusted under 35 U.S.C. 154(b) by 434 days.

(21) Appl. No.: 12/120,756

(22) Filed: May 15, 2008

(51) Int. Cl.
*A61K 31/4166* (2006.01)
(52) U.S. Cl. ...................................................... 514/389
(58) Field of Classification Search .................. None
See application file for complete search history.

(56) References Cited

U.S. PATENT DOCUMENTS 6,762,180 B1 * 7/2004 Roth et al. ................ 514/228.2
2005/0203156 A1 * 9/2005 Olson et al. ................... 514/389

OTHER PUBLICATIONS

Thenmozhiyal et al. J. Med. Chem., 2004, vol., 47, pp. 1527-1535.*
Sausville et al. Cancer Research, 2006, vol. 66, pp. 3351-3354.*
Johnson et al. British J. of Cancer, 2001, 84(10):1424-1431.*
Khanfar et al. Bioorganic & Medicinal Chemistry, 2009, vol. 17, pp. 6032-6039.*
Mudit et al. Bioorganic & Medicinal Chemistry, 2009, vol. 17, pp. 1731-1738.*
Shah et al. (Mol. Cancer Ther., 2009, vol. 8, No. 3, pp. 509-520.*
Bahner et al. J. Med. Chem., 1969, vol. 12, p. 722 (Abstract attached).*
Caternina Carmi, Andrea Cavazzoni, Valentina Zuliani, Alessio Lodola, Fabrizio Bordi, Pier Vincenzo Plazzi, Roberta R. Alferi, Pier Grorgio Petronini and Marco Mor, 5-Benzylidene-hydantoins as new EGFR inhibitors with antiproliferative activity, Bioorganic & Medicinal Chemistry Letters 16, 2006; pp. 4021-4025.
Manuela Meusel and Michael Gütschow; Recent developments in hydantoin chemistry. A review; Organic preparations and procedures international; vol. 36, Issue 5; pp. 391-443, 2004.
Jeyanthi Chinnappa Thenmozhiyal, Peter Tsun-Hon Wong and Wai-Keung Chui, Anticonvulsant Activity of Phenylmethylenehydantoins: A Structure-Activity Relationship Study; Journal of Medicinal Chemistry, 2004, vol. 47, No. 6.
Hue H. Luu, Ruiwen Zhang, Rex C. Haydon, Elizabeth Rayburn, Quan Kang, Weike Si, Jong Kyung Park, Hui Wang, Ying Peng, Wei Jiang and Tong Chuan He; Wnt/β-Cantenin Signaling Pathway as Novel Cancer Drug Targets; Current Cancer Drug Targets, 2004, 4, pp. 653-671.

* cited by examiner

*Primary Examiner* — James D Anderson
(74) *Attorney, Agent, or Firm* — Jones, Walker, Waechter, Poitevent, Carrere & Denegre, LLP

(57) ABSTRACT

The present invention relates to methods of either treating or preventing cancer and novel compositions relevant to that treatment and prevention. More particularly, this invention relates to compounds which share features with (Z)-5-(4-hydroxybenzylidene)imidazolidine-2,4-dione and (Z)-5-(4-S-ethylbenzylidene)imidazolidine-2,4-dione and anti-cancer uses for those compounds. Embodiments of the present invention include methods that have anti-cancer effects including anti-metastatic, anti-growth, and anti-invasive activities.

17 Claims, 6 Drawing Sheets

| Organs | Vehicle | 1-treated | 2-treated |
|---|---|---|---|
| Seminal Vesicles | ++++ | ++ | + |
| Testis | ++++ | +++ | + |
| Lymph Nodes | +++ | ++ | + |
| Bone | ++++ | - | - |
| Lungs | ++ | - | - |
| Liver | ++ | - | - |
| Mesentary | ++ | - | - |
| Kidneys | ++ | - | - |
| Brain | ++ | - | - |

FIG. 5

ANTI-CANCER HYDANTOIN COMPOUNDS AND METHODS

STATEMENT REGARDING FEDERALLY SPONSORED RESEARCH OR DEVELOPMENT

The U.S. Government may have a paid-up license in this invention and the right in limited circumstances to require the patent owner to license others on reasonable terms as provided for by the terms of grant/contract numbers CA96534 (GVS) and P20PR16456 (KES) awarded by the National Institutes of Health.

BACKGROUND

Cancer is one of the leading causes of death in Americans. Drugs that can prevent or limit metastasis, growth, or invasive properties of cancer in mammals have the potential for life saving use in humans. Metastasis is one of the predominant factors in the mortality of cancer patients. Because few options exist for the treatment of metastatic disease, drugs that show potential for the prevention or treatment of cancer and metastasis in particular have great value.

Information relevant to attempts to address these problems can be found in US Patent Publication Numbers: US-20070066616 and U.S. Pat. No. 5,389,614-A1; and the following publications Tony Lee Perry, *Isolation and lead optimization of natural sunscreens from the marine sponge Laxosubrites* sp. A Master's Thesis, The University of Mississippi, 1998 (University of Mississippi Library) and 3,5-Diisopropylbenzylidene heterocyclic compound, Japanese Patent Office abstract of publication number 62-029570 (Kanegafuchi Chem Ind Co Ltd) application published Feb. 7th 1987, which are not admitted to be prior art with respect to the present invention by their mention in the background. However, none of the references have adequately solved the need for anti-metastatic, anti-growth, and anti-invasive cancer drugs. For the foregoing reasons there is a need for compounds that display activity against cancer cells including the specific activities described above, methods of producing these compounds, and methods for treating cancer cells with these compounds.

SUMMARY

The present invention addresses the needs described above by providing compounds and methods having anti-cancer effects and thus the potential for development into lifesaving and/or life prolonging anti-cancer treatments. The compounds and methods of this invention are useful as leads for the development of anti-cancer compounds and anti-cancer treatments in mammals. In particular, embodiments of the present invention show anti-cancer characteristics including anti-metastatic, anti-growth, and anti-invasive activities. However, it is not necessary for all embodiments of the invention to have all of the advantages of the invention. A method of treating and/or preventing cancer having features of the present invention comprises treating or preventing a form of cancer by administering to a mammalian patient in need of said treatment or prevention a therapeutic amount of a compound or a therapeutic amount of a pharmaceutically acceptable salt of the compound, wherein the compound is (Z)-5-(4-S-ethylbenzylidene)imidazolidine-2,4-dione; (Z)-5-[4-(2-thienyl)benzylidene]imidazolidine-2,4-dione; (Z)-5-(3-methoxy-4-(2-oxo-2-(pyrrolidin-1-yl)ethoxy)benzylidene) imidazolidine-2,4-dione; (Z)-5-(4-hydroxybenzylidene) imidazolidine-2,4-dione; (Z)-5-(3-methoxybenzylidene) imidazolidine-2,4-dione; (Z)-5-(4-N,N-diethylaminobenzylidene)imidazolidine-2,4-dione; (Z)-5-(2-ethoxybenzylidene)imidazolidine-2,4-dione; (Z)-5-(4-butoxybenzylidene)imidazolidine-2,4-dione; (Z)-5-(2-fluorobenzylidene)imidazolidine-2,4-dione; (Z)-5-(3-chloro-4-(prop-2-ynyloxy)-5-methoxy-benzylidene) imidazolidine-2,4-dione; (Z)-5-(3-bromo-4,5-diethoxybenzylidene)imidazolidine-2,4-dione; (Z)-5-(3-bromo-4-propoxy-5-methoxy-benzylidene)imidazolidine-2,4-dione; (Z)-5-(2,3-methylenedioxy-benzylidene) imidazolidine-2,4-dione; (Z)-5-(4-(3-methyl-butoxy)-benzylidene)imidazolidine-2,4-dione; (Z)-5-(3-chloro-4-propoxy-5-methoxy-benzylidene)imidazolidine-2,4-dione; (Z)-5-(3-fluoro-4-propoxy-5-methoxy-benzylidene)imidazolidine-2,4-dione; (Z)-5-(3-methoxy-4-(2-morpholin-4-yl-2-oxo-ethoxy)-benzylidene)imidazolidine-2,4-dione; (Z)-5-(4-(tert-butyloxy)-benzylidene)imidazolidine-2,4-dione; (Z)-5-(4-(methylthio)-benzylidene)imidazolidine-2,4-dione; (Z)-5-(3-fluoro-4-(prop-2-ynyloxy)-5-methoxy-benzylidene)imidazolidine-2,4-dione; or (Z)-5-(3-bromo-4-(prop-2-ynyloxy)-5-methoxy-benzylidene)imidazolidine-2,4-dione. A further method of treating and/or preventing cancer having features of the present invention comprises administering to a mammalian patient in need of cancer treatment or prevention a therapeutic amount of a compound represented by the general formula 1,

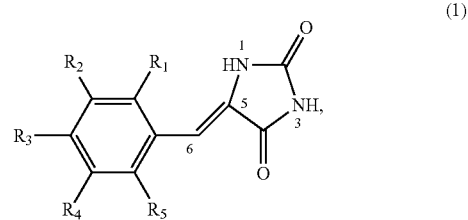

(1)

or a therapeutic amount of a pharmaceutically acceptable salt of the compound; wherein $R_1$ is H or $R_1$ is bound to the $R_2$ site by —$CH_2O$—$CH_2$—; wherein $R_2$ is selected from the group consisting of H, halo, alkoxy, aryloxy, acyloxy, and CN, or $R_2$ is bound to the $R_1$ site by —$CH_2O$—$CH_2$—; wherein $R_3$ is selected from the group consisting of H, hydroxyl, amine, alkylamine; thioalkyl, thioaryl, alkyl, alkenyl, alkynyl, aryl, cycloalkyl, heterocycloalkyl, aralkyl, heteroaryl, heteroaralkyl, alkoxy, aryloxy, acyloxy, CN, 1-(pyrrolidin-1-yl)alkanone, and acylamino; wherein $R_4$ is selected from the group consisting of H, halo, alkoxy, aryloxy, acyloxy, silyloxy, thiophene, and CN; and wherein $R_5$ is selected from the group consisting of H and halo. Preferably in the preceding method $R_1$ is hydrogen; $R_2$ is selected from the group consisting hydrogen, methoxy, and halo; $R_3$ is selected from the group consisting of ~OH, ~S—$CH_2CH_3$, ~H, ~N($C_2H_5$)$_2$, thioaryl, alkynyl, ~$OC_nH_{2n+1}$, 2-thienyl, prop-1-yne, and 1-(pyrrolidin-1-yl)ethanone; $R_4$ is selected from the group consisting of hydrogen, methoxy, ethoxy, butoxy, and bromide; $R_5$ is selected from the group consisting of hydrogen and fluorine; and "n" is a number selected from the group consisting of 2 and 3. Preferably in the preceding method any alkoxy, acyloxy, thioalkyl, or alkyl group present has between one and six carbon atoms; and any cycloalkyl group present has between three and eight carbon atoms. In a preferred embodiment of the preceding method each of $R_1$, $R_3$, $R_4$, and $R_5$ are hydrogen. In a different preferred embodiment of the preceding method each of $R_1$, $R_2$, $R_4$, and $R_5$ are hydrogen. In a further different preferred embodiment $R_1$, $R_2$, $R_3$, and $R_5$ are hydrogen. A method of treating and/or preventing cancer having features of the present invention additionally comprises either of the above mentioned methods wherein any of the aforementioned compounds and salts are used individually or in combination with one another. A composition of matter having features of the present invention comprises a compound selected from the group consisting of (Z)-5-(4-S-ethylbenzylidene)imidazolidine-2,4-dione; (Z)-5-[4-(2-thienyl)benzylidene]imidazolidine-2,4-dione; (Z)-5-(3-methoxy-4-(2-oxo-2-(pyrrolidin-1-yl)ethoxy)benzylidene)imidazolidine-2,4-dione; (Z)-5-(2,3-methylenedioxy-benzylidene)imidazolidine-2,4-dione; (Z)-5-(4-(3-methyl-butoxy)-benzylidene)imidazolidine-2,4-dione; (Z)-5-(3-chloro-4-propoxy-5-methoxy-benzylidene)imidazolidine-2,4-dione; (Z)-5-(3-fluoro-4-propoxy-5-methoxy-benzylidene)imidazolidine-2,4-dione; (Z)-5-(3-methoxy-4-(2-morpholin-4-yl-2-oxo-ethoxy)-benzylidene)imidazolidine-2,4-dione; and (Z)-5-(4-(tert-butyloxy)-benzylidene)imidazolidine-2,4-dione; or a salt of said compound. A composition of matter having features of the present invention additionally comprises any combination of the aforementioned compounds and salts.

BRIEF DESCRIPTION OF THE SEVERAL VIEWS OF THE DRAWINGS

FIG. 5 shows the presence of metastases in mice treated with either a vehicle, compound 1 or compound 2 based on xenograft testing with "−" indicating no cells present to "++++" indicating a large tumor mass.

DETAILED DESCRIPTION OF THE INVENTION

Figure 1:
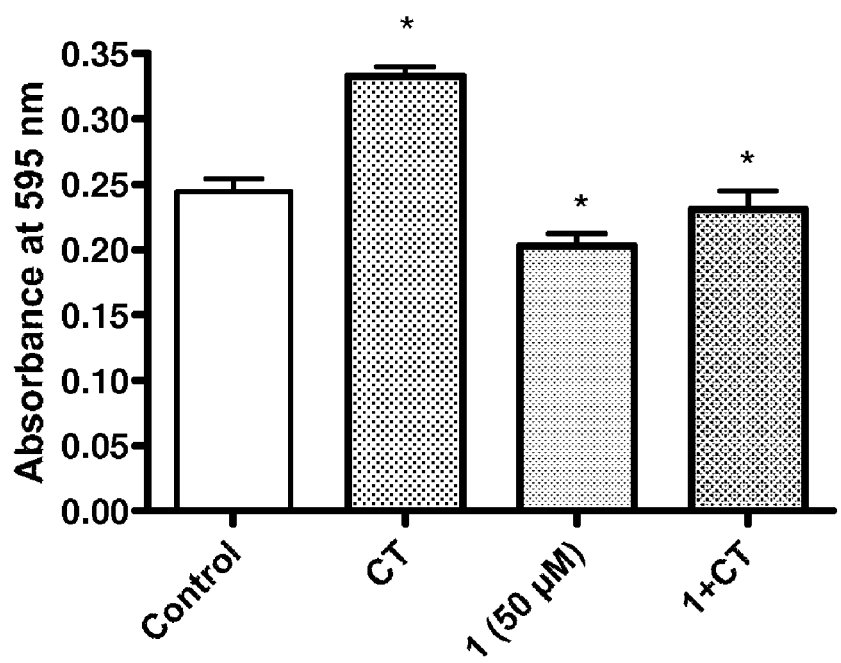
FIG. 1 shows MTT assay results for cell proliferation testing of a control group, a calcitonin (CT) stimulated group, a compound 1 treated group and a group that was both compound 1 treated and CT stimulated.

The compounds 1-12 as described below were either isolated or synthesized. These compounds were then tested for various activities pertinent to the treatment and/or prevention of cancer. In vitro testing was performed for cell growth, cell invasion, and spheroid disaggregation. In vivo testing was performed using xenografted and transgenic mice to test the effects of selected compounds. The compounds that follow are merely individual examples of the present invention and should not be construed to limit the scope of the invention either individually or as a group.

Compounds 1-12

(Z)-5-(4-hydroxybenzylidene)imidazolidine-2,4-dione referred to herein as compound 1 may be represented by the following chemical structure:

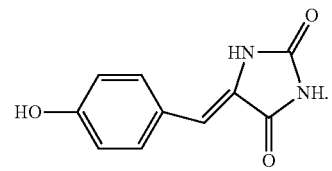

(Z)-5-(4-S-ethylbenzylidene)imidazolidine-2,4-dione referred to herein as compound 2 may be represented by the following chemical structure:

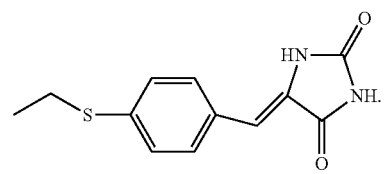

(Z)-5-(3-methoxybenzylidene)imidazolidine-2,4-dione referred to herein as compound 3 may be represented by the following chemical structure:

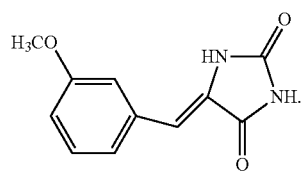

(Z)-5-(4-N,N-diethylaminobenzylidene)imidazolidine-2,4-dione referred to herein as compound 4 may be represented by the following chemical structure:

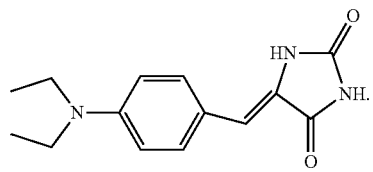

(Z)-5-[4-(2-thienyl)benzylidene]imidazolidine-2,4-dione referred to herein as compound 5 may be represented by the following chemical structure:

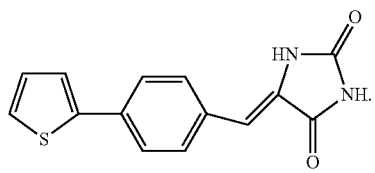

(Z)-5-(2-ethoxybenzylidene)imidazolidine-2,4-dione referred to herein as compound 6 may be represented by the following chemical structure:

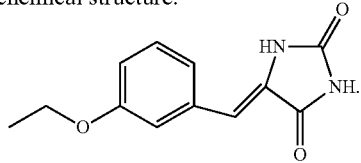

(Z)-5-(4-butoxybenzylidene)imidazolidine-2,4-dione referred to herein as compound 7 may be represented by the following chemical structure:

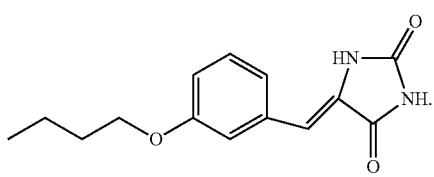

(Z)-5-(2-fluorobenzylidene)imidazolidine-2,4-dione referred to herein as compound 8 may be represented by the following chemical structure:

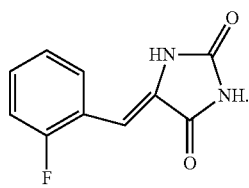

(Z)-5-(3-chloro-4-(prop-2-ynyloxy)-5-methoxy-benzylidene)imidazolidine-2,4-dione; referred to herein as compound 9 may be represented by the following chemical structure:

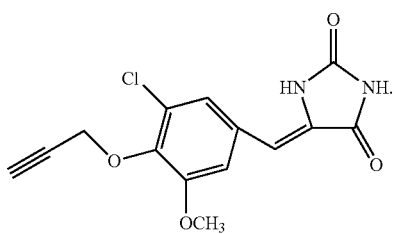

(Z)-5-(3-bromo-4,5-diethoxybenzylidene)imidazolidine-2,4-dione referred to herein as compound 10 may be represented by the following chemical structure:

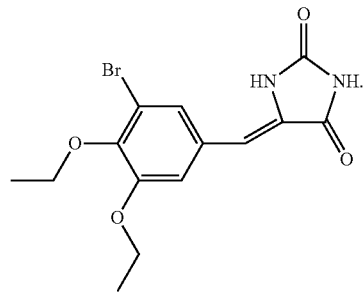

(Z)-5-(3-methoxy-4-(2-oxo-2-(pyrrolidin-1-yl)ethoxy)benzylidene)imidazolidine-2,4-dione referred to herein as compound 11 may be represented by the following chemical structure:

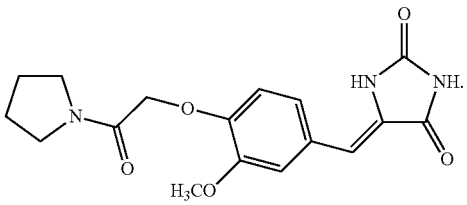

(Z)-5-(3-bromo-4-propoxy-5-methoxy-benzylidene)imidazolidine-2,4-dione referred to herein as compound 12 may be represented by the following chemical structure:

Additional Compounds

The immediately following descriptions are prophetic examples representative of further embodiments of the present invention and should not be construed to limit the scope of the invention either individually or as a group. Each of the compounds (Z)-5-(2,3-methylenedioxy-benzylidene) imidazolidine-2,4-dione; (Z)-5-(4-(3-methyl-butoxy)-benzylidene)imidazolidine-2,4-dione; (Z)-5-(3-chloro-4-propoxy-5-methoxy-benzylidene)imidazolidine-2,4-dione; (Z)-5-(3-fluoro-4-propoxy-5-methoxy-benzylidene) imidazolidine-2,4-dione; (Z)-5-(3-methoxy-4-(2-morpholin-4-yl-2-oxo-ethoxy)-benzylidene)imidazolidine-2,4-dione; (Z)-5-(4-(tert-butyloxy)-benzylidene)imidazolidine-2,4-dione; (Z)-5-(4-(methylthio)-benzylidene)imidazolidine-2,4-dione; (Z)-5-(3-fluoro-4-(prop-2-ynyloxy)-5-methoxy-benzylidene)imidazolidine-2,4-dione; and (Z)-5-(3-bromo-4-(prop-2-ynyloxy)-5-methoxy-benzylidene)imidazolidine-2,4-dione have structural properties including steric and charge properties similar to tested compounds which indicate that they could be prepared and employed in a manner similar to that of compounds 1-12.

The following descriptions represent structural embodiments of the present invention and should not be construed to limit the scope of the invention either individually or as a group. These structures and the compounds they represent have include tested compounds and compounds having structural properties including steric and charge properties similar to tested compounds which indicate that they could be employed in a manner similar to that of compounds 1-12. Compounds conforming to general formula 1 or pharmaceutically acceptable salts of those compounds wherein $R_1$ is H or $R_1$ is bound to the $R_2$ site by —$CH_2O$—$CH_2$—; wherein $R_2$ is selected from the group consisting of H, halo, alkoxy, aryloxy, acyloxy, and CN, or $R_2$ is bound to the $R_1$ site by —CH$_2$O—CH$_2$—; wherein R$_3$ is selected from the group consisting of H, hydroxyl, amine, alkylamine; thioalkyl, thioaryl, alkyl, alkenyl, alkynyl, aryl, cycloalkyl, heterocloalkyl, aralkyl, heteroaryl, heteroaralkyl, alkoxy, aryloxy, acyloxy, CN, 1-(pyrrolidin-1-yl)alkanone, and acylamino; wherein R$_4$ is selected from the group consisting of H, halo, alkoxy, aryloxy, acyloxy, silyloxy, thiophene, and CN; and wherein R$_5$ is selected from the group consisting of H and halo may be used in methods consistent with the various embodiments of this invention. Preferably R1 is hydrogen; R2 is selected from the group consisting hydrogen, methoxy, and halo; R3 is selected from the group consisting of ~OH, ~S—CH2CH3, ~H, ~N(C$_2$H$_5$)$_2$, thioaryl, alkynyl, ~OCnH2n+1, 2-thienyl, prop-1-yne, and 1-(pyrrolidin-1-yl)ethanone; R4 is selected from the group consisting of hydrogen, methoxy, ethoxy, butoxy, and bromide; R5 is selected from the group consisting of hydrogen and fluorine; and "n" is a number selected from the group consisting of 2 and 3. Preferably any alkoxy, acyloxy, thioalkyl, or alkyl group present has between one and six carbon atoms; and any cycloalkyl group present has between three and eight carbon atoms. In a preferred embodiment each of R1, R3, R4, and R5 are hydrogen. In a different preferred embodiment each of R1, R2, R4, and R5 are hydrogen. In a further different preferred embodiment R1, R2, R3, and R5 are hydrogen.

Figure 6:
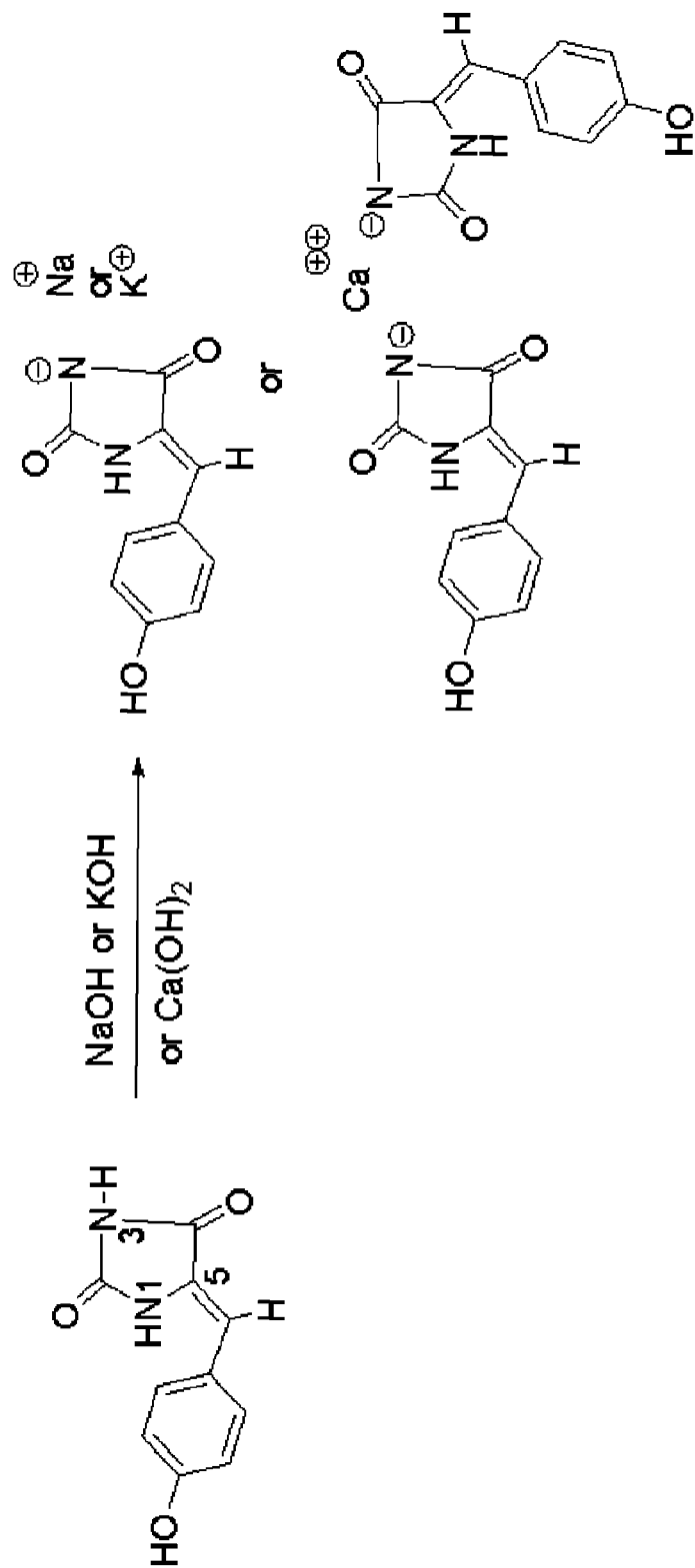
FIG. 6 shows an example of how sodium, potassium and/or calcium salts of compound 1 may be prepared.

Compounds of the invention may take the form of salts. Examples of salts which may be formed include sodium, potassium and/or calcium salts of hydantoins. Such salts may be prepared by using controlled additions of equimolar concentration of sodium hydroxide, potassium hydroxide or calcium hydroxide. The examples of salts provided are illustrative and a person having ordinary skill in the art would recognize the wide range of salts that could be formed based on the teachings herein and the compounds taught above. The reaction shown in FIG. 6 is an example of salts that have been prepared and is illustrative of how salts can be formed using compound 1 as an example. In certain instances, such as that of compound 12, the sodium salt of the compound has shown indications of higher efficacy than that of the compound in non-salt form.

Preparation of compounds 1-12

The synthesis of compounds 1-12 can be described generically by the following one step condensation reaction.

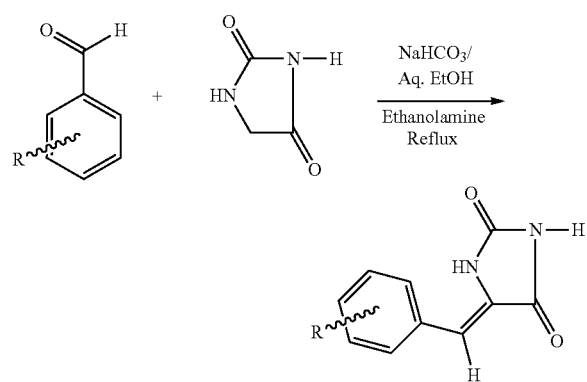

The procedure for the synthesis of various substituted phenylmethylene hydantoin derivatives follows. Hydantoin (1 gm) was dissolved in 10 ml of water in round-bottom flask at 70° C. with continuous stirring. After complete dissolution of the hydantoin, the pH was adjusted to 7.0 using saturated NaHCO$_3$. The temperature was further raised to 90° C. with the help of an oil bath after addition of ethanolamine (0.9 mL). An equimolar quantity of the suitable aldehyde solution in ethanol was added drop wise with continuous stirring, and then the temperature was raised to 120° C. Selection of the proper aldehyde will be obvious to one having ordinary skill in the art. For example, compound 1 is synthesized using 4-hydroxybenzaldehyde as the aldehyde. The reaction was kept under reflux conditions at this temperature for approximately 5-8 hours which usually depends on the nature of the aldehydic solution. Simultaneously, the course of reaction was monitored after regular interval of time with the help of TLC. Generally, the progression of the reaction towards its completion is evident by seeing the colored precipitate. After that, the mixture was cooled and the precipitate was filtered which was followed by washing with alcohol/water (1:5) in order to remove the soluble impurities before recrystallization using ethanol.

Preparation of Additional Compounds

Compounds and groups of compounds of the prophetic examples above may be prepared using the same general procedure described above for the preparation of compounds 1-12. As with compounds 1-12 selection of the appropriate aldehyde will be apparent to a person having ordinary skill in the art.

EXAMPLES

Several tests were performed on various compounds of the invention to evaluate the efficacy of the compounds. In vitro testing included MTT assays, invasion assays, and spheroid disaggregation or metastasis assays. In vivo testing included testing on xenografted nude mice and testing on transgenic mice. PC-3M prostate cancer cell line was used for screening because the cell line, isolated from liver metastasis of PC-3 xenografts, is highly metastatic, displays characteristics of androgen-refractory and highly metastatic prostate cancer and responds to calcitonin (CT) with increase in cell proliferation, invasion and metastasis.

Example 1

MTT Assays

MTT assays were used to measure effect of the tested drugs on tumor growth. MTT assays were performed on a control group, a calcitonin (CT) stimulated group, a group treated with compound 1 (drug treated), and a group that was both drug treated and CT stimulated. Conditions for the MTT assay were as follows: Exponentially growing cells were plated in a 96-well plate at a density of 8×10$^3$ cells per well, and cultured for 24 hours in complete growth medium (RPMI 1640 containing 10% fetal bovine, 10 mM HEPES, 4 mM L-glutamine, 100 IU/ml penicillin G and 100 µg/ml streptomycin). The complete growth medium was then replaced with 100 µl of basal incubation medium (RPMI 1640 containing 0.1% BSA, 10 mM HEPES, 4 mM L-glutamine, 100 IU/ml penicillin G and 100 µg/ml streptomycin). The cells were then treated with test compounds (dissolved in basal incubation medium), and the culture was continued at 37° C. under 5% CO$_2$ for 24 hours. The cells were then treated with MTT solution at 37° C. for 4 h, and the color reaction was stopped with the stop solution (10% sodium dodecyl sulfate solution in 0.01 M hydrochloric acid) (100 μl/well). The incubation at 37° C. was continued until the formazan product was completely dissolved. Absorbance of the samples was determined at 595 nm with an ELISA plate reader (Bio-Rad, Hercules, Calif.).

Compound 1 was found to be effective in limiting baseline and CT-stimulated cell proliferation of PC-3M cells based on MTT assay results. FIG. 1 shows that 50 μM of compound 1 caused a moderate but significant decline in the rate of baseline and CT stimulated cell proliferation. Compound 1 did not display any cytotoxic effect on PC-3M cells until a dosage rate of 500 μM, or 10 times the effective dosage rate of 50 μM.

Example 2

Invasion Assays

Invasion assays were used to identify compounds with antimetastatic activity. Invasion assays were performed on a control group, a calcitonin (CT) stimulated group, a drug treated group and a group that was both drug treated and CT stimulated. The assay employed two-compartmented Boyden invasion chambers sold under the trademark MATRIGEL. The assay conditions were as follows: exponentially growing PC cells were serum-starved for 24 hours with basal incubation medium. Serum-starved cells were then seeded at a density of $25 \times 10^3$ cells/well in the upper insert of the invasion chamber. The lower chamber received the chemoattractant medium, which consisted of 90% basal RPMI medium and 10% conditioned medium from the cultures of PC-3M cells expressing constitutively active Gsa protein as described in Chien, J., Wong, E., Nikes, E., Noble, M. J., Pantazis, C. G., and Shah, G. V. (1999) *Oncogene* 18(22), 3376-3382 which is incorporated herein by reference. The incubations were carried out for 24 hours, after which the basement matrix protein or Matrigel™ (along with non-invading cells) was scraped off with cottonswabs, and the outer side of the insert was fixed and stained using hemaoxylin staining sold under the trademark Diff Quick (Dade Behring Diagnostics, Aguada, PR). The number of cells migrated on the outer bottom side of the insert were counted under the microscope in six or more randomly selected fields (magnification: 100×). The final results were expressed as mean+/−SEM number of invaded cells per 100× field. Each experiment was done in triplicates, and the experiment was repeated twice. Since some PC-3M cell sublines exhibited higher proliferation rate, It was considered as a possibility that the cells that migrated during the early part of the 24-hour incubation period could proliferate during the remaining period of incubation, causing a slight overestimation of the final results. To correct this, the growth rate was determined for PC-3M cells under identical culture conditions. $25 \times 10^3$ cells were plated at hourly intervals in six-well dishes and cultured for 1-24 hours. Mean percent increase in the cell number was determined by counting the net increase in the number of cells. The relative CT-induced increase of the pooled results of all time points was found to be 1.19 (vehicle control=1). This correction was applied to the results of invasion assays.

Figure 2:
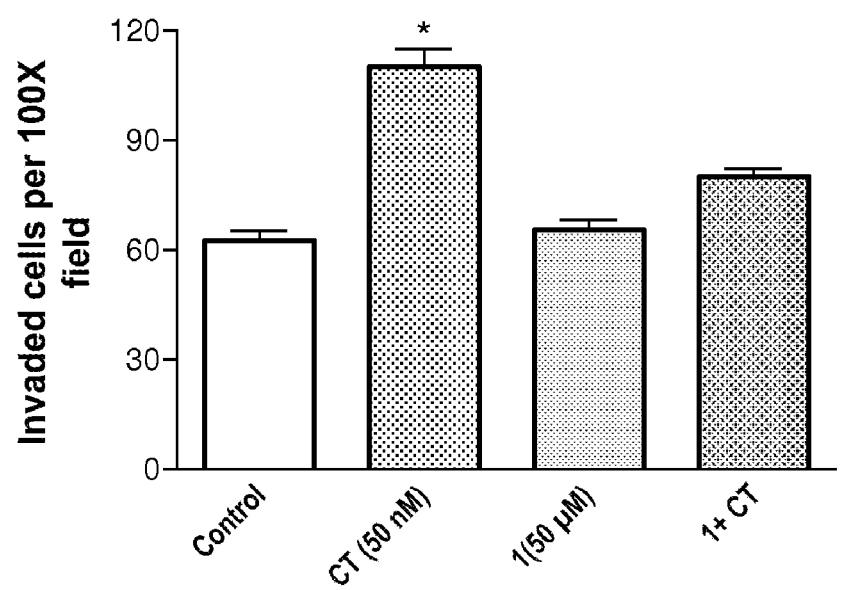
FIG. 2 shows invasion assays results for cell invasion testing of a control group, a calcitonin stimulated group, a compound 1 treated group and a group that was both compound 1 treated and CT stimulated.

Compound 1 was also found to be effective in limiting the CT-stimulated invasion of PC-3M cells. FIG. 2 shows that CT (50 nM) significantly increased the invasion of PC-3M cells, compound 1 (50 μM) did not affect baseline invasion but almost abolished CT-stimulated invasion.

Example 3

Metastasis Assays

In vitro metastasis assays were conducted to determine the anti-metastatic effect of various compounds. This assay involves preparation of spheroids approximately 50 μm in diameter of cancer cells cultured on an extracellular matrix. In 24 hours, only metastatic cells disaggregate from the spheroid and start radial migration. Thus, lower measurements of radial migration are indicative of greater effectiveness of the drug/compound. Spheroids were prepared from single cell suspension of prostate cell lines as described before in Gondi, C. S., Lakka, S. S., Yanamandra, N., Olivero, W. C., Dinh, D. H., Gujrati, M., Tung, C. H., Weissleder, R., and Rao, J. S. (2004) *Cancer Res* 64(12), 4069-4077 and in Thomas, S., Chiriva-Internati, M., and Shah, G. V. (2007) *Clin Exp Metastasis* 24(5), 363-377 both of which are incorporated herein by reference. $5 \times 10^4$/ml cells in RPMI 1640 serum-free medium were placed on 96-well low-attachment tissue culture plates. The plates were rocked on gyrotory shaker in a $CO_2$ incubator at 37° C. for 2 days, at the end of which the spheroids measuring 150-300 μm in diameter (~$4 \times 10^4$ cells/spheroid) were formed. A single spheroid was then placed in the center of each well of extracellular-matrix-coated 24-well microplate in 200 ml of serum-free medium. From previous studies, it was determined that 1 hour was an appropriate time for spheroids to begin adhering to an extracellular matrix. Thus, t=0 was set as 1 hour from initial plating, so that if the plate was not disturbed, the spheroids would not move from their location at the time of plating. Spheroids were digitally photographed at t=0, cultured at 37° C. for 48 h and then re-photographed. The spheroids were then fixed, stained with hemaoxylin staining sold under the trademark Diff-Quik (Dade Behring, Newark, Del.) and examined under light microscopy. The diameter of the area covered with cells migrated from the spheroids was measured in a microscope calibrated with a stage and ocular micrometer. The radial distance of migration was calculated after subtraction of the mean initial spheroidal diameter at t=0.

Figure 3:
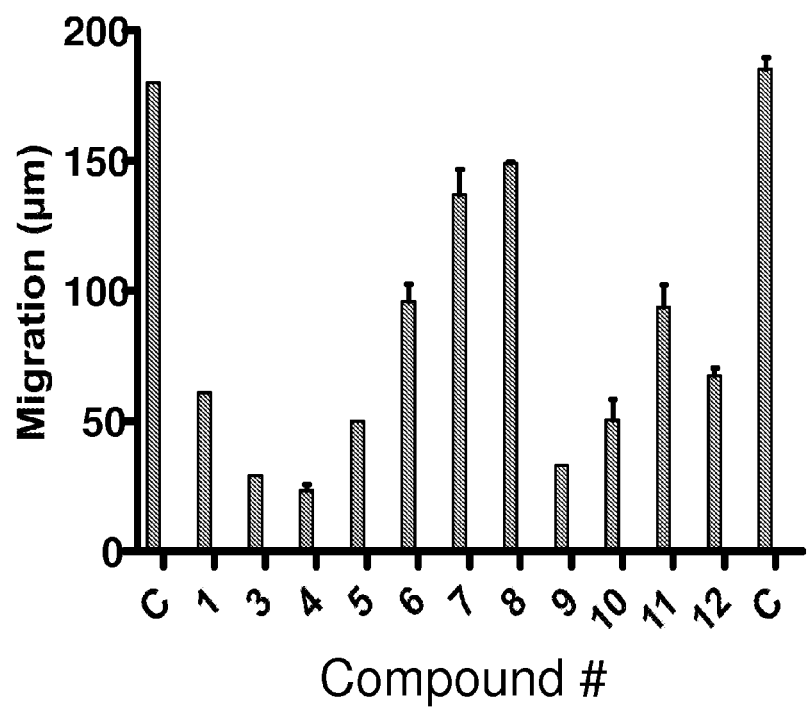
FIG. 3 shows migration distance in a metastasis assay for compounds 1 and 3-12.

When the spheroids were incubated in the presence of compound 1 (50 μM), the cells remained within the spheroid and did not disaggregate or migrate, suggesting that the drug can potentially be used for preventing metastasis. The treatment was repeated with multiple doses of compound 1 and measured the distances migrated by the cells at the end of the experiment. The effective dose range of the drug was 25-200 μM and the drug did not exhibit cytotoxicity until a 500 μM dose. FIG. 3 shows migration distance in the described metastasis assay for various other compounds and controls. Dosing for the tests displayed in FIG. 3 were 100 μM for Compound 1 and 200 μM for all remaining compounds. The result in FIG. 3 for compound 12 is the result of testing with the sodium salt of compound 12.

Example 4

Xenograft Testing

In vivo xenograft testing was done on athymic nude mice to measure the anti-cancer effect of various compounds. PC-3M prostate cells were used that contain a red fluorescence protein from gene transfer to facilitate tracking of cancer cells. The red fluorescence protein used is described in Yang, M., Baranov, E., Wang, J. W., Jiang, P., Wang, X., Sun, F. X., Bouvet, M., Moossa, A. R., Penman, S., and Hoffman, R. M. (2002) *Proc Natl Acad Sci U S A* 99(6), 3824-3829, which is incorporated herein by reference. $1 \times 10^5$ PC-3M cells over expressing CT were implanted in 30 day old mice orthotopically, that is the prostate cancer cells were implanted into the prostate of the mice. The cells were then allowed to grow in their native environment allowing for metastasis into other organs such as the lymph nodes, bones and lungs. The mice, other than the control mice were injected intraperitoneally every other day. Dosing rates were 200 µg/day or 5 µg/g body weight/day-intrapertonieally for compound 1 and 40 µg/day or 1 µg/g body weight/day-intraperitoneally for compound 2. Tumor growth was measured by fluorescence imaging and the mice were sacrificed upon signs of morbidity such as immobility and high tumor burden.

Figure 4:
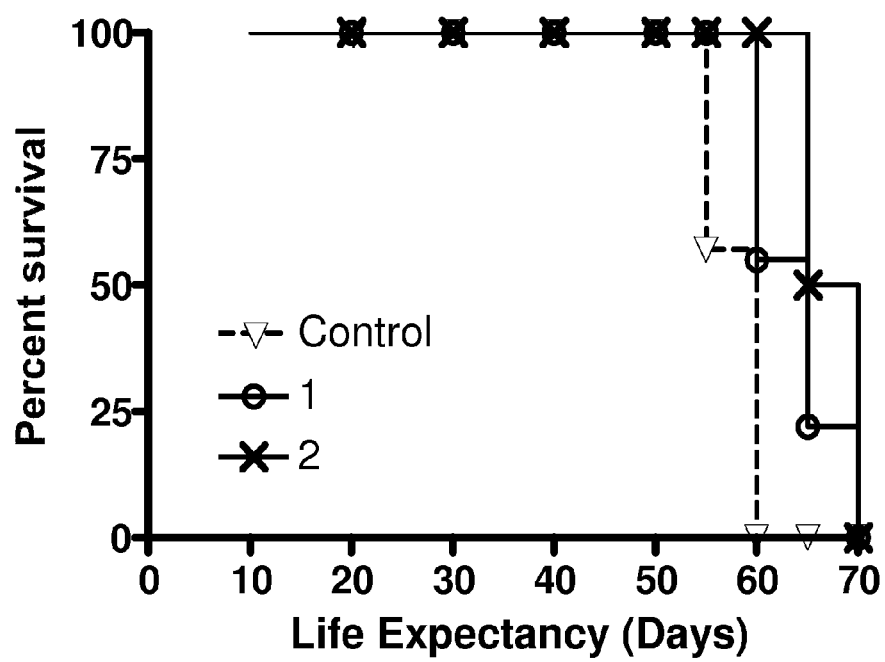
FIG. 4 shows the survival rates of xenografted mice comparing the use of compounds 1 and 2 to a control.

The average life-expectancy of untreated mice was 54 days±1.13 SEM (n=6), which increased to 61.44 days±1.06 SEM (n=9) when treated with compound 1, and increased further to 66±1 SEM (n=3) when treated with compound 2. Survival curves for the mice are presented in FIG. 4. Compounds 1 and 2 completely prevented tumor growth in most secondary organs. FIG. 5 shows the presence of metastases in mice treated with either a vehicle, compound 1 or compound 2 based on xenograft testing. Organs were harvested and observed for fluorescent cells grading the metastases from "−" indicating no cells present to "++++" indicating a large tumor mass. FIG. 5 shows the results of that grading.

Example 5

Testing of Transgenic Mice

In vivo testing was done on transgenic mice that spontaneously form prostate tumors to measure the anti-cancer effect of compound 2. The mice used were LPB-Tag mice of the type described in Kasper, S., and Smith, J. A., Jr. (2004) *J Urol* 172(1), 12-19 which is incorporated herein by reference. The mice were originally developed by Dr. Robert Matusik of Vanderbilt University. LPB-Tag mice are generated by the targeted expression of SV40 large T-antigen (Tag) in the prostate using androgen-regulated, prostate-specific large probasin (LPB) gene promoter. The mice develop PIN lesions as well as extensive prostate adenocarcinomas in adulthood. The mice had their p53 gene knocked out and T-antigen selectively targeted to the prostate. Therefore, the mice begin to develop prostate tumors spontaneously as they approached the age of 50 days (adulthood), the tumors gradually grew and became very large at the age of 90 days. Mice were sacrificed around day 90 and their prostates and other organs were harvested for studying tumor characteristics and histology. Compound 2 was delivered at a dosing of 80 µg/week or 2 µg/g body weight/week-intraperitoneally. Tumor size for compound 2 treated mice measured at necropsy was decreased by 62% compared to diluents treated mice and compound 2 treated mice displayed increased survival of at least 1 week. These tests indicate that compounds of this invention may be used as a chemopreventive for high risk patients.

As used herein the term "pharmaceutically acceptable salt" refers to a salt prepared from any one or multiple non-toxic acid(s) or base(s) including both organic and inorganic acids and bases that is suitable for use in contact with living animal or human tissue without causing adverse physiological responses.

As used herein the term "therapeutic amount" indicates an amount which is sufficient to effect beneficial or desired clinical results.

The various compounds disclosed herein as embodiments of the invention may be used in vivo in a manner similar to the examples teaching the in vivo use of compounds 1 and 2. These compounds may be used for the treatment or prevention of any of the various forms of cancer. They are preferably used in the treatment or prevention or of prostate, breast, pancreatic and ovarian cancer; and most preferably used in the treatment or prevention of prostate cancer. Treatment or prevention of forms of cancer other than prostate cancer may be carried out using tests similar to the tests disclosed herein. Such tests will be apparent to a person of ordinary skill in the art based on the disclosure herein. Therapeutically effective dosages rates may be determined by animal testing similar to the testing of examples 4 and 5. In a prophetic embodiment of the invention compounds described herein preferably have dosing rates between 0.2 and 20 mg/kg body weight weekly and most preferably have dosing rates between 2 and 20 mg/kg body weight weekly.

The compounds disclosed herein may be administered in any pharmaceutically acceptable form including, but not limited to, intravenous, oral, subcutaneous, intramuscular, intradermal, intraperitoneally, and parenteral. The route of administration will preferably be designed to optimize delivery and/or localization of the agents to target cells.

administered to a patient by any conventional route of administration,

As is apparent to those skilled in the art in light of the foregoing disclosure, many alterations and modifications are possible in the practice of this invention without departing from the spirit or scope thereof. Aspects of the various embodiments of the invention may be interchanged in whole or in part. The spirit and scope of the invention should not be limited to the description of the preferred versions contained herein. Accordingly, the invention should be construed as defined by the following claims.

We claim:

1. A method of treating prostate cancer comprising administering to a mammalian patient in need of said treatment a first therapeutic amount of a compound or a second therapeutic amount of a pharmaceutically acceptable salt of said compound, wherein said compound is selected from the group consisting of:
  (Z)-5-(4-S-ethylbenzylidene)imidazolidine-2,4-dione;
  (Z)-5-[4-(2-thienyl)benzylidene]imidazolidine-2,4-dione;
  (Z)-5-(3-methoxy-4-(2-oxo-2-(pyrrolidin-1-yl)ethoxy) benzylidene)imidazolidine-2,4-dione;
  (Z)-5-(4-hydroxybenzylidene)imidazolidine-2,4-dione;
  (Z)-5-(3-methoxybenzylidene)imidazolidine-2,4-dione;
  (Z)-5-(4-N,N-diethylaminobenzylidene)imidazolidine-2,4-dione;
  (Z)-5-(2-ethoxybenzylidene)imidazolidine-2,4-dione;
  (Z)-5-(4-butoxybenzylidene)imidazolidine-2,4-dione;
  (Z)-5-(2-fluorobenzylidene)imidazolidine-2,4-dione;
  (Z)-5-(3-chloro-4-(prop-2-ynyloxy)-5-methoxy-benzylidene)imidazolidine-2,4-dione;
  (Z)-5-(3-bromo-4,5-diethoxybenzylidene)imidazolidine-2,4-dione;
  (Z)-5-(3-bromo-4-propoxy-5-methoxy-benzylidene)imidazolidine-2,4-dione;
  (Z)-5-(2,3-methylenedioxy-benzylidene)imidazolidine-2,4-dione;
  (Z)-5-(4-(3-methyl-butoxy)-benzylidene)imidazolidine-2,4-dione;
  (Z)-5-(3-chloro-4-propoxy-5-methoxy-benzylidene)imidazolidine-2,4-dione;
  (Z)-5-(3-fluoro-4-propoxy-5-methoxy-benzylidene)imidazolidine-2,4-dione;
  (Z)-5-(3-methoxy-4-(2-morpholin-4-yl-2-oxo-ethoxy)-benzylidene)imidazolidine-2,4-dione;
  (Z)-5-(4-(tert-butyloxy)-benzylidene)imidazolidine-2,4-dione;
  (Z)-5-(4-(methylthio)-benzylidene)imidazolidine-2,4-dione;
  (Z)-5-(3-fluoro-4-(prop-2-ynyloxy)-5-methoxy-benzylidene)imidazolidine-2,4-dione; and (Z)-5-(3-bromo-4-(prop-2-ynyloxy)-5-methoxy-benzylidene)imidazolidine-2,4-dione.

2. The method of claim 1 wherein said compound is (Z)-5-(4-S-ethylbenzylidene)imidazolidine-2,4-dione.

3. The method of claim 1 wherein said compound is (Z)-5-[4-(2-thienyl)benzylidene]imidazolidine-2,4-dione.

4. The method of claim 1 wherein said compound is (Z)-5-(3-methoxy-4-(2-oxo-2-(pyrrolidin-1-yl)ethoxy)benzylidene)imidazolidine-2,4-dione.

5. The method of claim 1 wherein said compound is (Z)-5-(4-hydroxybenzylidene)imidazolidine-2,4-dione.

6. The method of claim 1 wherein said compound is (Z)-5-(3-methoxybenzylidene)imidazolidine-2,4-dione.

7. The method of claim 1 wherein said compound is (Z)-5-(4-N,N-diethylaminobenzylidene)imidazolidine-2,4-dione.

8. The method of claim 1 wherein said compound is (Z)-5-(2-ethoxybenzylidene)imidazolidine-2,4-dione.

9. The method of claim 1 wherein said compound is (Z)-5-(4-butoxybenzylidene)imidazolidine-2,4-dione.

10. The method of claim 1 wherein said compound is (Z)-5-(2-fluorobenzylidene)imidazolidine-2,4-dione.

11. The method of claim 1 wherein said compound is (Z)-5-(3-chloro-4-(prop-2-ynyloxy)-5-methoxy-benzylidene)imidazolidine-2,4-dione.

12. The method of claim 1 wherein said compound is (Z)-5-(3-bromo-4,5-diethoxybenzylidene)imidazolidine-2,4-dione.

13. The method of claim 1 wherein said compound is (Z)-5-(3-bromo-4-propoxy-5-methoxy-benzylidene)imidazolidine-2,4-dione.

14. The method of claim 1 wherein said compound is selected from the group consisting of:
(Z)-5-(2,3-methylenedioxy-benzylidene)imidazolidine-2,4-dione;
(Z)-5-(4-(3-methyl-butoxy)-benzylidene)imidazolidine-2,4-dione;
(Z)-5-(3-chloro-4-propoxy-5-methoxy-benzylidene)imidazolidine-2,4-dione;
(Z)-5-(3-fluoro-4-propoxy-5-methoxy-benzylidene)imidazolidine-2,4-dione;
(Z)-5-(3-methoxy-4-(2-morpholin-4-yl-2-oxo-ethoxy)-benzylidene)imidazolidine-2,4-dione;
(Z)-5-(4-(tert-butyloxy)-benzylidene)imidazolidine-2,4-dione;
(Z)-5-(4-(methylthio)-benzylidene)imidazolidine-2,4-dione;
(Z)-5-(3-fluoro-4-(prop-2-ynyloxy)-5-methoxy-benzylidene)imidazolidine-2,4-dione; and
(Z)-5-(3-bromo-4-(prop-2-ynyloxy)-5-methoxy-benzylidene)imidazolidine-2,4-dione.

15. The method of claim 1 wherein said first therapeutic amount is between 0.2 and 20 mg/kg body weight weekly and wherein said second therapeutic amount is between 0.2 and 20 mg/kg body weight weekly.

16. A method of treating prostate cancer comprising administering to a mammalian patient in need of said treatment a first therapeutic amount of a compound represented by the general formula:

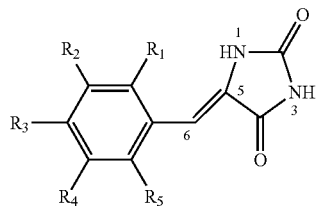

or a second therapeutic amount of a pharmaceutically acceptable salt of said compound;
wherein $R_1$ is hydrogen;
wherein $R_2$ is selected from the group consisting hydrogen, methoxy, and halo;
wherein $R_3$ is selected from the group consisting of —OH, ~S—$CH_2CH_3$, ~H, ~$N(C_2H_5)_2$, thioaryl, alkynyl, ~$OC_nH_{2n+1}$, 2-thienyl, prop-1-yne, and 1-(pyrrolidin-1-yl)ethanone;
wherein $R_4$ is selected from the group consisting of hydrogen, methoxy, ethoxy, butoxy, and bromide;
wherein $R_5$ is selected from the group consisting of hydrogen and fluorine; and
wherein "n" is a number selected from the group consisting of 2 and 3.

17. A method according to claim 16 wherein each of $R_1$, $R_3$, $R_4$, and $R_5$ are hydrogen.

* * * * *